United States Patent [19]

Doyle et al.

[11] Patent Number: 5,527,415

[45] Date of Patent: * Jun. 18, 1996

[54] INTRAOCULAR LENSES AND METHODS FOR PRODUCING SAME

[75] Inventors: Christopher E. Doyle, Irvine; Bernard F. Grisoni, Aliso Viejo; Richard S. Graham, Irvine, all of Calif.

[73] Assignee: Allergan, Inc., Irvine, Calif.

[ * ] Notice: The term of this patent shall not extend beyond the expiration date of Pat. No. 5,423,929.

[21] Appl. No.: 412,657

[22] Filed: Mar. 28, 1995

Related U.S. Application Data

[63] Continuation of Ser. No. 143,798, Oct. 27, 1993, Pat. No. 5,423,929.

[51] Int. Cl.$^6$ ................................................. B32B 31/00
[52] U.S. Cl. .................. 156/250; 156/272.2; 156/273.3; 156/293; 156/329; 623/6
[58] Field of Search .................................. 156/293, 329, 156/245, 272.2, 73.1, 250, 273.3; 623/6

[56] References Cited

U.S. PATENT DOCUMENTS

| | | |
|---|---|---|
| 3,296,161 | 1/1967 | Kulpa . |
| 3,382,205 | 5/1968 | Beers . |
| 3,776,829 | 12/1973 | Goan . |
| 3,994,027 | 11/1976 | Jensen et al. . |
| 4,025,965 | 5/1977 | Siegmund . |
| 4,212,719 | 7/1980 | Osada et al. . |
| 4,307,043 | 12/1981 | Chase et al. . |
| 4,312,575 | 1/1982 | Peyman et al. . |
| 4,499,148 | 2/1985 | Coodale et al. . |
| 4,502,163 | 3/1985 | Graham . |
| 4,609,420 | 9/1986 | Aydin et al. . |
| 4,615,702 | 10/1986 | Koziol et al. . |
| 4,619,662 | 10/1986 | Juergens, Jr. . |
| 4,662,882 | 5/1987 | Hoffer . |

(List continued on next page.)

FOREIGN PATENT DOCUMENTS

| | | |
|---|---|---|
| 141705 | 6/1986 | Japan . |
| 2180757 | 4/1987 | United Kingdom . |
| 9004512 | 5/1990 | WIPO . |
| WO9200708 | 1/1992 | WIPO . |
| 9314924 | 8/1993 | WIPO . |

OTHER PUBLICATIONS

Chawla, A. S., Use of Plasma Polymerization for Preparing Silicone–Coated Membranes for Possible Use in Blood Oxygenators, Artificial Organs vol. 3, No. 1, 1979.

Evans et al, Introduction of Functional Groups onto Carbon Electrodes via Treatment with Radio–Frequency Plasmas, Analytical Chemistry, vol. 51 No. 3, 1979.

Donnet et al, Plasma Treatment Effect on the Surface Energy of Carbon and Carbon Fibers, Carbon vol. 24, No. 6, pp. 757–770, 1986.

Cormia et al, "Use Plasmas To Re–engineer Your Advanced Materials", R & D Magazine, Jul. 1990.

(List continued on next page.)

*Primary Examiner*—David A. Simmons
*Attorney, Agent, or Firm*—Frank J. Uxa

[57] ABSTRACT

New intraocular lenses (IOLs) and methods for producing IOLs are disclosed. The present methods include a combination of steps which increase the pull strength between the fixation member of the IOL and the optic of the IOL without requiring sophisticated high frequency corona discharge activation or plasma activation of the fixation member. The fixation members are doubly coated with primer components and silicone polymeric material precursor compositions before being secured to the optics. In addition, the optic members employed in the present invention can be formed, for example, molded, without recesses to accommodate the fixation members. Thus, such recesses can be formed and provided with a quantity of the above-noted precursor composition after the optic members are produced. The doubly coated fixation members are then placed in the recesses and secured to the optic members. The present methods are straight forward, easy to practice and are cost effective in producing high quality IOLs.

19 Claims, 1 Drawing Sheet

U.S. PATENT DOCUMENTS

| | | |
|---|---|---|
| 4,668,446 | 5/1987 | Kaplan et al. . |
| 4,701,288 | 10/1987 | Cook et al. . |
| 4,702,865 | 10/1987 | Koziol et al. . |
| 4,718,905 | 1/1988 | Freeman . |
| 4,735,623 | 4/1988 | Hatzenbuhler . |
| 4,735,632 | 4/1988 | Katzenbuhler . |
| 4,737,322 | 4/1988 | Bruns et al. . |
| 4,743,327 | 5/1988 | DeHaan et al. . |
| 4,790,846 | 12/1988 | Christ et al. . |
| 4,834,751 | 5/1989 | Knight et al. . |
| 4,854,999 | 8/1989 | Schirmer . |
| 4,888,013 | 12/1989 | Ting et al. . |
| 4,936,849 | 6/1990 | Knoll et al. . |
| 5,032,209 | 7/1991 | Shinbach . |
| 5,069,926 | 12/1991 | Iwata et al. . |
| 5,080,924 | 1/1992 | Kamel et al. . |
| 5,104,590 | 4/1992 | Blake . |
| 5,126,164 | 6/1992 | Okazaki et al. . |
| 5,147,397 | 9/1992 | Christ et al. . |
| 5,185,107 | 2/1993 | Blake . |

OTHER PUBLICATIONS

Osada et al, "Plasma–Initiated Graft Polymerization of Water–Soluble Vinyl Monomers Onto Hydrophobic Films and Its Application to Metal Ion Adsorbing Films", Thin Solid Films, 118(1984) 197–202.

Sipehia et al, "Enhanced albumin Binding to polypropylene beads via anhydrous ammonia gaseous plasma", Biomaterials 1986 vol. 7 Nov.

Suzuki, et al, Graft Copolymerization of Acrylamide onto a Polyethylene Surface Pretreated with a Glow Discharge, Macromolecules 1986, 19, 1804–1808.

Sakata et al, Corona–Induced Graft Polymerization of Ethyl Acrylate onto Cellulose Film, Journal of Applied Polymer Science vol. 20, 573–579 (1976).

Wrobel et al, Polymerization of Organosilicones in Microwave Discharges, J. Macromol, Sci. Chem. A14(3), pp. 321–337 (1980).

INTRAOCULAR LENSES AND METHODS FOR PRODUCING SAME

This application is a continuation of application Ser. No. 08/143,798, filed Oct. 27, 1993, now U.S. Pat. No. 5,423,929.

BACKGROUND OF THE INVENTION

This invention relates to intraocular lenses (IOLs) and to methods for producing IOLs. More particularly, the present invention relates to relatively straight forward and easy to practice methods for producing IOLs with optics comprising silicone polymeric materials and to such IOLs which have advantageous properties, for example, increased fixation member pull strengths, that is increased bond strengths between the optic of the IOL and the fixation member or members of the IOL.

The use of IOLs to improve vision and/or to replace damaged or diseased natural lenses in human eyes, particularly natural lenses impaired by cataracts, has achieved wide acceptance. Accordingly, a variety of IOLs has been developed for surgical implantation in the posterior or anterior chambers of the eye according to a patient's needs.

Known IOLs comprise an optical lens portion or optic which includes an optical zone, and one or more, preferably two, supporting structures, called fixation members or haptics, for contacting eye tissue to fix or hold the IOL in the proper position after implantation. The optic may comprise a soft, resilient material, such as a silicone polymeric material (in particular, an elastomeric silicone polymeric material) or a relatively hard or rigid material such as, for example, polymethylmethacrylate (PMMA). The haptics typically comprise a filament constructed of a resilient metal or polymeric substance, such as PMMA, polyimide or polypropylene.

Each of the filament haptics is preferably flexible to reduce trauma to sensitive eye structures and to be yielding during insertion of the IOL. In addition, filament haptics generally have a memory retaining capability, e.g., springiness, so that after implantation of an associated IOL, the filament haptics automatically tend to return to their normal orientation.

As an alternative to filament haptics, some IOLs are provided with footplate-type haptics. These footplates generally extend radially outwardly from the optic (in the plane of the optic) and terminate in rounded or blunted ends configured for placement in an eye chamber. The materials for such footplates have included soft materials, for example, 2-hydroxyethyl methacrylate or silicone. However, footplate-type haptics are attended by disadvantages, such as the addition of extra material weight to the IOL and reduced flexibility as compared to filament haptics leading to poor fixation and consequent migration or dislocation of the IOL.

Although the filament haptics are preferred over the footplate-type haptics for several reasons, certain difficulties remain. For example, filament haptics and soft or deformable optics tend to be formed from dissimilar materials which do not ordinarily chemically bond together. As a result, filament haptics have been designed having a variety of attachment end configurations or structures, e.g., anchor structures, for providing a physical or mechanical interlock between the haptic and optic. Polypropylene haptics, for example, have heretofore been secured into silicone polymer-based optics by means of a mechanical lock. This lock may comprise a small loop or other anchor formed at the attachment end or lens bonding region of the haptic, which is then placed in a mold. The precursor material of the silicone polymer-based optic is poured into the mold, through and/or around the lens bonding region of the included haptic or haptics, and is then cured. Christ et al U.S. Pat. No. 4,790,846 discloses the molding of an optic around a haptic having a small loop or other anchor to effect a secure haptic connection.

Christ et al U.S. Pat. No. 4,790,846 further discloses a method for making an IOL in which a region of an elongated filament haptic has a different configuration, e.g., a bulbous enlargement, which cooperates with the optic of the IOL to form a mechanical interlock between this different configuration and the optic. If desired, the bulbous enlargement may have its outer surface roughened to improve adhesion of the material of the optic.

Bruns et al U.S. Pat. No. 4,737,322 discloses an IOL including haptics with anchoring struts which are located in the optic and surround or partially surround the center of the optical zone portion of the optic. These struts provide sufficient anchoring of the haptic in the optic to withstand a tensile pull force of from 50 to 115 grams.

Blake et al U.S. Pat. No. 5,104,590 discloses improving the adhesive properties of polypropylene haptics to silicone lenses through surface treatment of the haptic with a combination of a high frequency corona discharge and a silicone primer. Christ et al U.S. Pat. No. 5,147,397 discloses exposing the lens bonding region of a haptic to a plasma at conditions effective to enhance the bondability of the lens bonding region to the optic. While these procedures can be effective in enhancing haptic/optic bond strength, they are relatively sophisticated and are relatively expensive to practice, thus adding to the complexity and cost of producing IOLs. In addition, substantial care must be exercised in controlling the corona discharge and plasma exposing procedures to avoid damaging the relatively fine filament haptics.

It would be advantageous to provide a relatively straight forward and easy to practice method of producing IOLs which effectively enhances the bond or pull strength between the fixation member or members and the optic.

SUMMARY OF THE INVENTION

New methods for producing IOLs and new IOLs have been discovered. The present production methods are relatively straight forward, easy to practice and cost effective, and provide IOLs which have enhanced or increased fixation member pull strengths. Thus, the amount of force required to separate the fixation member from the optic of an IOL produced as set forth herein is increased relative to a substantially identical IOL which is not made in accordance with the present invention. Further, this increase in pull strength is achieved with little or no risk of detrimentally affecting the intrinsic strength and other advantageous properties of the fixation member in producing the IOL. It has been found that increased fixation member pull strengths are achieved without requiring activation of the fixation member surface with high frequency corona discharge or plasma. The present methods very reliably, predictably and reproducibly produce high quality IOLs.

In addition, since in accordance with the present invention the optic is formed prior to joining the fixation member or members to the optic, the conditions at which the optic is formed can be chosen to optimize the properties of the optic without consideration for possible damage to the relatively fine filament haptic. Also, relatively low melting point materials of construction can be used in the fixation members. Moreover, the cost of the IOL is reduced, for example, because simplified optic molding or other optic forming procedures can be employed. Increased flexibility in molding cycle time and curing temperature, and increased interchangeability in the mold tooling required for optic forming results because the fixation member is not present when the optic is being formed. This increased flexibility and interchangeability, in turn, increase production capacity and/or reduce capital and product development costs.

The present IOLs are relatively straight forward in construction, provide for little or no interference with the optical zone of the optic by the fixation member or members and have substantial fixation member/optic pull strengths. The present IOLs are preferably produced using the present IOL production methods.

In one broad aspect, the present invention is directed to methods for producing an IOL including an optic and at least one fixation member having a proximal end, or lens bonding region, located in the optic. The present methods comprise contacting the proximal end portion of a fixation member, which has not been subjected to either (or both) high frequency corona discharge activation or plasma activation, with a primer component to form a coated fixation member; contacting the proximal end portion of the coated fixation member with a precursor composition of a cross-linked silicone polymeric material to form a doubly coated fixation member; forming a recess in a pre-formed optic member which comprises a silicone polymeric material; placing the proximal end portion of the doubly coated fixation member into the recess; and subjecting the optic member and the doubly coated fixation member in the recess to conditions effective to cure the precursor composition. The present methods preferably further comprise forming the optic member, for example, using a mold. The proximal end portion of the fixation member is preferably made of a non-silicon-containing material and is preferably formed with no anchor structure or structures. In a more preferred embodiment, the fixation member has a length and has a substantially uniform cross-sectional area along its length. The use of a primer component on fixation members which have not been subjected to high frequency corona discharge activation or plasma activation in combination with the other steps of the present methods have been found to result in a very effective and straight forward approach to producing high quality IOLs with very advantageous properties.

In another broad aspect of the present invention, IOLs are provided which include an optic, a fixation member and a primer component or residue thereof. The optic member comprises a silicone polymeric material, preferably which is cross-linked. The fixation member includes a proximal end portion or lens bonding region formed with no anchor structure or structures and secured in the optic. This fixation member has been subjected to no high frequency corona discharge activation or plasma activation, and is preferably made of a non-silicon-containing material. The primer component or residue thereof is located between the fixation member and the optic. Such IOLs, which are preferably produced using the present IOL production methods, have increased fixation member/optic pull strength relative to a substantially identical IOL with no primer component or residue thereof present.

The invention, together with additional features and advantages thereof may best be understood by reference to the following description taken in connection with the accompanying illustrative drawings.

DETAILED DESCRIPTION OF THE INVENTION

Figure 1:
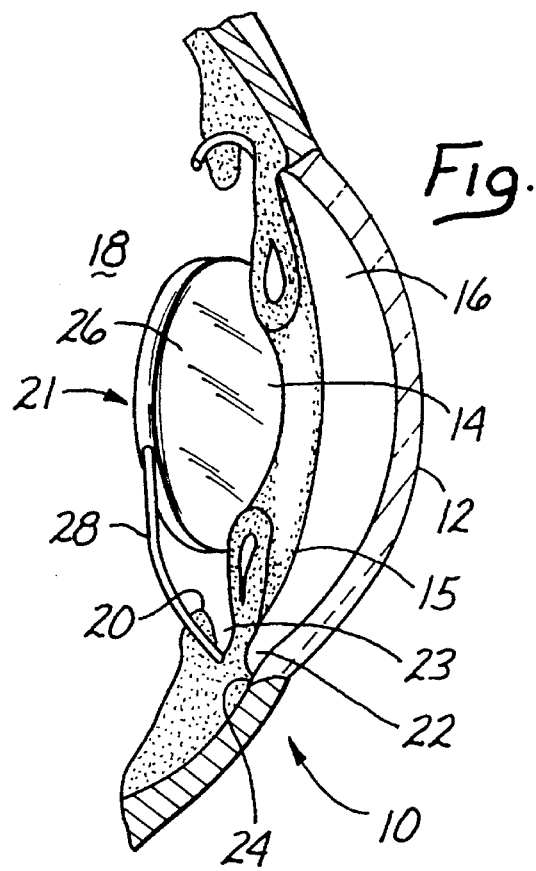
FIG. 1 is a simplified representation of the physiology of the human eye.

The present invention is based, in part, upon the discovery that the fixation member or members of an IOL can be attached or secured to the optic of the IOL with acceptably high pull strength without requiring possibly detrimental modification to the surface of the fixation member or members. In particular, satisfactory enhancement or increase in the pull strength of fixation member or members relative to the optic of an IOL is obtained without the fixation member being subjected to high frequency corona discharge activation or plasma activation. Because no such surface activation is required, the risk that such activation procedure will detrimentally affect the structure and other advantageous properties of the fixation member or members is eliminated.

The present methods produce IOLs including an optic, which has an optical zone through which light passes so that the wearer of the IOL has improved vision, and at least one fixation member, preferably two fixation members, having a proximal end portion or lens bonding region located in the optic.

The optic comprises a silicone polymeric material, for example, an elastomeric silicone polymeric material, which is preferably cross-linked. The optic may be derived from a two part silicone formulation which is introduced into a mold cavity at a weight ratio of about 1:1, as is known to one of skill in the art. Part A typically includes a catalyst and a base polymer. Part B typically includes a cross-linker and the same base polymer. The base polymer is preferably synthesized from siloxanes. In one particularly useful embodiment, the optic comprises a polymer which is a platinum-catalyzed, vinyl/hydride, addition cured poly-organosiloxane. One particularly useful optic composition includes a silicone polymeric material which is reinforced, for example, with an effective reinforcing amount of a suitable resin and/or silica. The present optics may include one or more other components in amounts effective to provide a beneficial property to the optic. For example, an effective amount of an ultraviolet light absorbing component may be included, preferably covalently bonded to the silicone polymeric material of the optic.

The present methods of producing IOLs preferably include forming an optic member. Although other suitable techniques may be employed to form the optic member, one particularly useful approach is to form a precursor composition and inject such precursor composition into a suitable mold. The precursor-containing mold is then subjected to effective conditions, for example, conventional silicone curing conditions, to cure the precursor composition into the desired silicone polymeric material. The cured material is then removed from the mold and is ready for additional processing in accordance with the present invention. Of course, pre-formed optic members can be provided from other sources and, therefore, the optic member forming need not be a part of the present methods.

One important preferred feature of the present invention is that the optic member is formed with no recess or recesses for insertion of the fixation member or members. This feature, in which the optic member as formed includes no recess or recesses for the fixation member or members, greatly simplifies the procedure by which the optic member is formed. For example, in the molding approach, the mold does not have any additional wires or other means by which recesses for the fixation members are incorporated into the formed optic member. Also, since no such recesses are formed and the fixation member or members are not included during the optic member forming step, there is no concern with the fixation member or members at this point in the method. Thus, there is more flexibility in the mold cycle time and curing temperature, and more interchangeability in the mold tooling. This, in turn, increases production capacity and reduces capital, operating and other costs. Also, since the fixation member or members are not exposed to prolonged curing conditions, a wider variety of fixation member materials of construction, for example, including low melting materials of construction, can be employed.

Each fixation member typically comprises a flexible member comprising metal or, preferably, polymeric material, and has a substantially circular cross-section, although alternate cross-sectional configurations may be substituted, if desired. The cross-sectional area of the present fixation members is preferably substantially uniform along the length of the fixation member or members. The fixation members have sufficient strength to provide support for the IOL in the eye. The fixation members may comprise any of a variety of materials which exhibit sufficient supporting strength and resilience and which are substantially biological inert in the intended in vivo environment. Suitable materials for this purpose include, for example, polymeric materials such as polypropylene, PMMA, polycarbonates, polyamides, polyimides, polyacrylates, 2-hydroxymethyl-methacrylate, poly (vinylidine fluoride), polytetrafluoroethylene and the like; and metals such as stainless steel, platinum, titanium, tantalum, shape-memory alloys, e.g., nitonal, and the like. More preferably the fixation member or members comprise a polymeric material, such as those selected from polypropylene, PMMA and polyimides, especially extruded PMMA and polypropylene. The fixation members can be produced using conventional and well known forming techniques. For example, the preferred polymeric fixation members can be formed in accordance with known thermoplastic polymer forming techniques, such as by injection molding or by extrusion.

The present methods for producing IOLs include contacting the proximal end portion or lens bonding region of the fixation member with a primer component at conditions effective to form a coated fixation member. This coated fixation member includes an effective (to ultimately provide enhanced fixation member/optic member pull strength) coating of primer component located on the proximal end portion of the fixation member. The primer component coating is effective to enhance the bond strength between the proximal end portion and a silicone polymeric object (for example, the optic member) to which the proximal end portion is bonded. This enhancement is relative to a substantially identical proximal end portion without the coating of primer component. The fixation member is subjected to no high frequency corona discharge activation and to no plasma activation.

The primer component employed in the present invention may be any suitable such primer material or combination of such primer materials which function as described herein to produce a final IOL having increased pull strength between the fixation member and the optic relative to a substantially similar IOL in which the primer material or combination of primer materials is not employed. Many primer materials are conventional, well known in the art and commercially available. Without wishing to limit the present invention to any particular theory of operation, it is believed that the primer component interacts with or otherwise conditions the proximal end position, for example, the surface of the proximal end portion, of the fixation member to render it more compatible or susceptible to being bonded to an optic member comprising a silicone polymeric material.

In one useful embodiment, the primer component is selected from silanes or orthosilicates, metal-containing components and mixtures thereof. Examples of useful primer components include organo silanes or orthosilicates, such as silanes including alkoxy groups and/or substituted alkoxy groups each having 1 to about 6, preferably 1 to about 4, carbon atoms (or orthosilicates including alkyl groups or substituted alkyl groups each having 1 to about 6, preferably 1 to about 4, carbon atoms); organo titanium-containing components, such as titanates including alkyl groups or substituted alkyl groups each having 1 to about 6, preferably 1 to about 4, carbon atoms; and mixtures thereof. Such alkoxy groups include methoxy, ethoxy, propoxy, butoxy, pentoxy, hexoxy and the like. Such alkyl groups include methyl, ethyl, propyl, butyl, pentyl, hexyl and the like. As used herein the terms "substituted alkoxy group" and "substituted alkyl group" refer to the alkoxy group and the alkyl group, respectively, in which at least one of the H atoms has been replaced by another species, e.g., group, including one or more atoms of elements such as carbon, hydrogen, oxygen, silicon, nitrogen, sulfur, phosphorus and the like and mixtures thereof.

Specific useful primer components include products containing one or more of tetra(2-methoxyethoxy) silane, tetrapropylorthosilicate and tetrabutyltitanate, such as materials sold by NuSil Technology under the trademarks CF1-135, CF2-135 and CF6-135, and the material sold by Dow Corning under the trademark Dow 1200. Mixtures of these materials are also useful.

The coated fixation member should have a sufficient amount of the primer component so as to yield an IOL having increased fixation member/optic pull strength, as described herein. The primer component may be present in an amount in the range of about 0.1% or less to about 50% or more of the weight of that portion of the fixation member that is coated with the primer component.

In a particularly useful embodiment, the proximal end portion of the fixation member is dipped in or otherwise contacted with a liquid medium containing the primer component, for example, for a time in the range of about 0.5 second to about 2 minutes, preferably about 0.5 second to about 30 seconds, so as to form a coating on the proximal end portion of the fixation member. After this coating is formed, the coated fixation member is exposed to conditions to dry or otherwise remove the liquid medium from the coating, leaving a coating comprising the primer component on the proximal end portion of the fixation member. Care should be taken in removing the liquid medium not to do so at conditions which would detrimentally affect the chemical makeup and/or functioning of the primer component. In most instances, the removal of the liquid medium can be accomplished at room temperatures or at temperatures below about 40° C. The coated fixation member is preferably maintained at conditions effective to remove the liquid medium for a period of time in the range of about 1 minute to about 60 minutes or more, more preferably in the range of about 2 minutes to about 20 minutes. Very useful results are obtained when the proximal end portion of the fixation member is dipped in the liquid medium containing the primer component for about 1 second, and the coated fixation member is subjected to drying or liquid medium removal conditions for about 5 minutes.

The primer component is preferably soluble in the liquid medium employed. The liquid medium is preferably non-aqueous-based. Particularly useful results are obtained employing organic components, for example, hydrocarbon-based components, as the liquid medium or carrier for the primer components. Examples of useful organic components include naphtha, lower alkanols (such as propanol and butanol), glycols and mixtures thereof. The primer component may comprise about 1% or less to about 10% or more by weight of the primer component/liquid medium mixture.

The proximal end portion of the coated fixation member is dipped in or otherwise contacted with a precursor composition of a cross-linked silicone polymeric material so as to form a doubly coated fixation member. Thus, the proximal end portion of the fixation member has an inner coating of primer component and an outer coating of the above-noted precursor composition. The coating of precursor composition is preferably present in an amount effective to react with residual reactable groups in the optic member (while the precursor composition is being cured, as described herein). Thus, the cross-linked polymer produced from the precursor composition forms a strong adhesive bond to the silicone polymeric material of the optic member. The precursor composition coating may be present in an amount in the range of about 10% or less to about 100% or more by weight of the length of the fixation member coated by the precursor composition. This precursor composition may be chosen from those conventionally employed in producing cross-linked silicone-polymeric materials, for example, for use in IOLs. In a particularly useful embodiment, the precursor composition used to form the doubly coated fixation member has substantially the same chemical make-up or composition as the precursor composition from which the optic member is formed.

As noted above, the formed optic member does not include any recess or recesses into which the fixation member or members can be placed. In order to accommodate the fixation member or members, a recess or recesses is separately formed in the pre-formed or already formed optic member. Such recess or recesses have a size sufficient to accept the proximal end portion of the doubly coated fixation member or members. In a particularly useful embodiment, the recess forming step comprises puncturing the optic member with a needle-like implement, and removing the needle-like implement from the optic member. The needle-like implement is preferably coated with the above-noted precursor composition before being used to puncture the optic member. This coating facilitates the puncturing operation, and produces a recess having a wall at least partially coated with the precursor composition. This, in turn, facilitates the enhanced bonding of the doubly coated fixation member or members to the optic body.

Once the recess has been formed in the optic member, the proximal end portion of the doubly coated fixation member is placed in the recess. With the doubly coated fixation member in place, the optic member and doubly coated fixation member are subjected to conditions effective to cure the precursor composition of the cross-linked polymeric material located on the fixation member. Such conditions are substantially as conventionally used to cure such precursor compositions and form cross-linked silicone polymeric materials and include an elevated temperature, for example, in the range of about 40° C. to about 100° C. However, the time during which such curing takes place is relatively limited because of the relatively limited amount of precursor composition to be cured. The subjecting step preferably forms an intraocular lens assembly in which the pull strength of the fixation member is increased, preferably by at least about 20% and more preferably by at least about 50%, relative to a substantially identical intraocular lens assembly formed by a substantially identical method without the primer component contacting step described herein.

The subjecting step may leave the primer component unaffected, or may change its chemical make-up resulting in the formation of a residue (or derivative) of the primer component. In any event, whether the primer component or a residue thereof (or a mixture of primer component and residue) is present, the intraocular lens assembly (and final IOL) has increased fixation member/optic member (optic) pull strength, preferably increased by at least about 20% and more preferably by at least about 50%, relative to a substantially identical intraocular lens assembly (or final IOL) without the primer component and/or residue thereof present.

After this subjecting step, the resulting intraocular lens assembly may be subjected to additional procedures, for example, conventional lens finishing procedures to produce the final IOL.

An additional important advantage of the present invention is the predictability and reproducibility of the present methods. Thus, in order for a method of producing IOLs to be commercially effective, the method should produce IOLs which have reliably and predictably reproducible properties, for example, to avoid the production of undue amounts of waste materials and to improve cost effectiveness.

The present methods produce IOLs which have fixation member/optic pull strengths with a standard deviation (defined in a conventional manner) from the mean fixation member/optic pull strength of a plurality of such IOLs produced in accordance with the present methods of less than about 15%, preferably less than about 10%, of the mean pull strength. This outstanding predictability and reproducibility of the present methods lends itself to commercial practice since the IOLs produced have properties which have acceptable fixation member/optic pull strengths and can be reliably produced while producing reduced amounts of scrap product.

Without wishing to limit the invention to any particular theory of operation, it is believed that the predictability and reproducability of the present methods are directly linked to the relatively straight forward and unsophisticated nature of the present methods. For example, since no high frequency corona discharge activation or plasma activation of the fixation member surface is involved in the present methods, the variability which almost inherently is introduced because of such activation procedures is not present in the present methods. The compositions of the optic member, of the fixation member, of the primer component, and of the precursor composition of a cross-linked silicone composition can be very reliably set and controlled. Also, the size of the recess in the formed optic member can be very effectively controlled. In effect, each of the steps of the present methods is relatively easy to effectively control resulting in an intraocular lens assembly which has reliable, predictable and reproducible properties.

Particularly useful silicone polymeric materials for use as optic member materials of construction are reinforced elastomeric compositions including polysiloxane elastomers, preferably having the chemical composition of a cross-linked copolymer including about 12 to about 18 mol percent of aryl substituted siloxane units of the formula $R_4R_5$—SiO where the aryl substituents ($R_4$ and $R_5$ groups) can be independently selected from phenyl groups, mono-lower alkyl substituted phenyl groups, and di-lower alkyl substituted phenyl groups. Preferably, both aryl groups are simple phenyl, and the resulting diphenyl siloxane unit is present in the copolymer in an amount of about 14 to about 18 mole percent.

The copolymer is end blocked with trisubstituted (monofunctional)siloxane units. At least one substituent of the end blocking group contains an olefinic bond. Thus, the general formula of the end blocking group incorporated in the copolymer is $R_1R_2R_3SiO_{0.5}$ where the nature of the $R_1$ and $R_2$ is not critical, and they may be independently selected from, for example, alkyl, aryl, substituted alkyl and substituted aryl groups. $R_3$ contains an olefinic bond. $R_3$ is preferably an alkenyl group, more preferably a vinyl group. In a preferred embodiment, the end blocking group is a dimethyl, vinyl siloxane unit. The role of the olefinic (vinyl) group is to enable curing or cross-linking of the polymer, and preferably covalently linking certain ultraviolet light absorbing compounds to the cross-linked copolymer matrix.

The balance of the siloxane building blocks of the copolymer is preferably dialkyl siloxane units wherein the two alkyl substituents are either ethyl or methyl. In other words, the general formula of the balance of the siloxane building blocks of the copolymer is preferably $R_6R_7$—SiO where the $R_6$ and $R_7$ groups are independently selected from methyl and ethyl. Preferably both $R_6$ and $R_7$ groups are methyl.

The copolymer may have a degree of polymerization (dp) of about 100 to about 2000, although a degree of polymerization of about 250 is preferred, particularly when the $R_4$ and $R_5$ groups are phenyl and the $R_6$ and $R_7$ groups are methyl.

The preparation of the copolymer having the above described components can be performed in accordance with processes known in the art, from starting materials which are either commercially available or can be made in accordance with well known processes.

The elastomeric silicone composition preferably contains a reinforcer, for example, a fume silica reinforcer, such as trimethylsilyl treated silica reinforcer, finely dispersed therein.

The reinforcer, for example, the fume silica reinforcer, is preferably used in an amount of about 15 to about 45 parts by weight of the reinforcer to 100 parts of the copolymer. Fume silica itself is commercially available. The fume silica reinforcer preferably used has a surface area of about 100 to about 450 meter$^2$/gram. More preferably, the fume silica has a surface area of about 200 meter$^2$/gram, is present in an amount (by weight) of about 27 parts (by weight) to 100 parts (by weight) of the copolymer, and is trimethylsilylated with hexamethyldisilazane substantially in the same step where the copolymer is intimately mixed with the silica.

The intimate mixture of the fume silica with the copolymer is commonly termed the "base" in the art. For the purpose of making materials suitable for intraocular lens, the base may be dispersed in a suitable inert solvent, such as trichlorotri-fluoroethane, and the dispersion filtered to remove any solid impurities. Thereafter, the solvent is removed by gentle heat and vacuum.

In accordance with standard practice in the art, the base is divided into two aliquots which preferably are of equal weight. The aliquots are commonly termed "Part A" and "Part B".

Silicon bonded hydride groups are added to the second aliquot (Part B) in the form of cross-linking agents, which are conventional and well known in the art. The liquid organohydrogen polysiloxane cross linkers having the formula $(R)_a(H)_b SiO_{4-a-b/2}$ wherein R is simple lower alkyl, for example, methyl, and a ranges from about 1.00 to about 2.10 and b ranges from about 0.1 to about 1.0, are eminently suitable.

The platinum catalyst can be selected from materials which are conventional and well known in the art.

The cross-linking should not proceed too rapidly at room temperature, thereby allowing at least two, preferably about six hours for work time with the mixed aliquots. For this reason, a suitable cross-linking inhibitor, such as 1, 2, 3, 4 tetramethyl-1,2, 3, 4-tetravinyl cyclotetrasiloxane, may be added to the second aliquot (Part B).

Formation of the optic members may be accomplished by liquid injection molding, or by cast or compression molding of the intimately mixed Parts A and B. The coated fixation member can be dipped in and/or otherwise contacted with intimately mixed Parts A and B, with or without the reinforcer component being present, to form the doubly coated fixation member useful in producing the present IOLs.

Referring now to FIG. 1, there is depicted the in vivo placement into an eye 10 of an IOL 21 according to the present invention, in which lens bonding regions of the haptics have been doubly coated prior to being inserted into recesses formed into the already formed optic member.

The cornea 12 serves as a refractory medium in addition to its function as the anterior wall of the eye 10. The pupil 14 and the iris 15 of variable aperture are located behind the cornea 12 and divide the eye into an anterior chamber 16 and a posterior chamber 18. The natural crystalline lens (not illustrated) is connected by zonular fibers to a peripheral muscle about the lens known as the ciliary muscle 20.

The surgical implantation of IOL 21 is accomplished by an incision in the eye, removal of the diseased or damaged natural lens (if applicable) an insertion of the IOL into the eye, the optic 26 of IOL 21 includes a centrally located optical zone and may be configured for implantation into a specific one or either of the anterior or posterior chambers 16 or 18. The haptics 28 of IOL 21 extend radially outwardly in the general plane of the optic 26.

A peripheral limit of anterior chamber angle 22 exists between the base of the iris 15 and a scleral spur, which serves as a support location for IOL 21 implanted within the anterior chamber 16 of the eye 10. A peripheral zone 23 also exists within the posterior chamber 18 between the ciliary muscle 20 and the base of the iris 15, which is known as the ciliary sulcus 24. The peripheral zone 23 serves as a mountain location for IOL 21 within the posterior chamber 18. Referring to FIG. 1, IOL 21 is shown positioned in the posterior chamber 18 and is supported by the haptics 28 bearing upon the ciliary sulcus 24.

Figure 2:
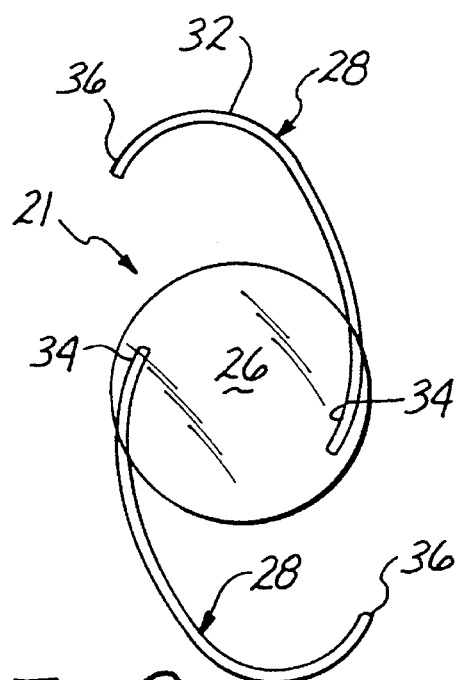
FIG. 2 is a plan view of an IOL in accordance with the present invention.
Figure 3:
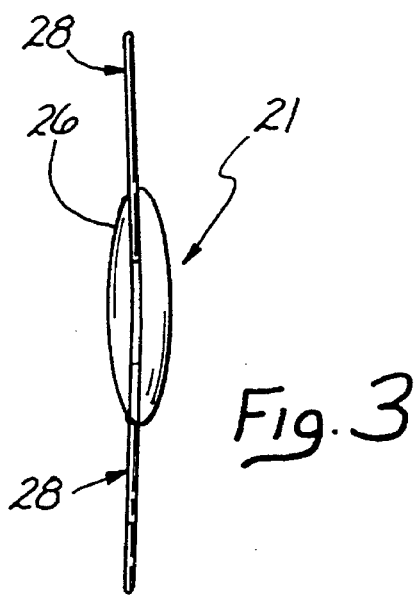
FIG. 3 is a side view of the IOL of FIG. 2.

Referring now to FIGS. 2 and 3, IOL 21 is illustrated as including a pair of radially outwardly extending haptics 28 secured to optic 26. The optic 26 is made of an optically clear, silica reinforced, platinum-catalyzed, vinyl/hydride addition cured (cross-linked) polyorganosiloxane polymer and has an index of refraction (refractive index) of about 1.46. Each haptic 28 has a substantially uniform cross sectional area throughout its length and is shown provided with a smoothly curved region 32, intermediate a lens bonding region 34 and a free end region 36. Although the illustrated embodiment is provided with two opposing haptics 28, it is understood that an IOL having only haptic or more than two haptics bonded to the optic by the method disclosed herein is considered within the scope of the invention.

Figure 4:
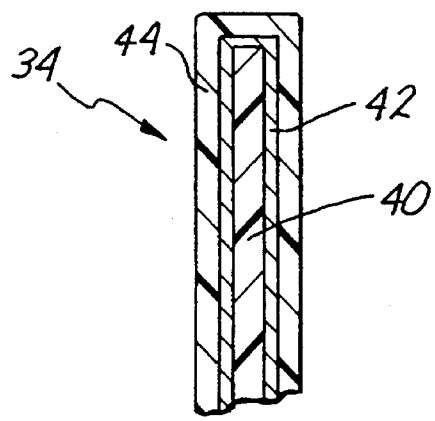
FIG. 4 is a partial cross-sectional view of a doubly coated fixation member of the present invention.

Referring now to FIG. 4, the lens bonding region 34 of haptic 28 is shown in more detail. In particular, as shown in FIG. 4, lens bonding region 34 is shown as it exists prior to it being inserted into the optic 26. Lens bonding region 34 includes the base haptic 40 which is made of extruded PMMA and extends from the lens bonding region 34 to the free end region 36 of haptic 28. A first coating 42 of a primer component, such as described elsewhere herein, is located directly in contact with base haptic 40. Such first coating 42 may be applied to base haptic 40 as described elsewhere herein. In addition, a second coating 44 comprising a precursor composition of a cross-linked silicone polymeric material is located on first coating 42. The precursor composition has the same chemical make-up as the precursor from which the optic 26 is produced. This second coating 44 may be applied to first coating 42 as described elsewhere herein. It should be noted that although the entire base haptic 40 can be doubly coated as described herein, preferably only the lens bonding region 34 which is to be located in optic 26 is doubly coated.

The lens bonding region 34 as shown in FIG. 4 is ready for insertion into a separately formed recess in optic 26.

IOL 21 is produced in accordance with the present invention, as described herein. Briefly, the optic 26 is formed with no recesses to accommodate the haptics 28 by conventional molding techniques from a cross-linked silicone polymeric material. The base haptic 40 is coated with a liquid medium containing the primer component and dried to remove the liquid medium. This coated base haptic is recoated with precursor composition to form the lens bonding region 34 as shown in FIG. 4. Recesses are formed in formed optic 26 to accommodate the lens bonding regions 34 of haptics 28. Such recesses may be formed, for example, by puncturing optic 26 to an appropriate depth and at an appropriate location with a needle or a machine tool, such as a drill and the like, or by using photoablation, ultrasound or a water jet. The recesses formed have a size sufficient to accommodate the doubly coated lens bonding region 34. A quantity of the precursor composition is placed in each of the recesses. If a needle is used to form the recesses, it can be coated with the precursor composition. Alternately, a pin coated with the precursor composition can be introduced into the recess to at least partially coat the walls of the recess with the precursor composition. If desired, the precursor composition can be injected into the recess. The lens bonding regions 34 of the haptics 28 are placed in such recesses and the entire assembly is subjected to silicone polymer curing conditions to secure the haptic 28 to the optic 26. The assembled optic 26/haptics 28, which has increased haptic/optic pull strength relative to a substantially identical assembly produced without the primer component, may be further processed, for example, using one or more conventional lens finishing techniques, and packaged ready for shipment. IOL 26 may be implanted in the eye 10 using conventional techniques. After implantation, IOL 21 functions very effectively.

The following non-limiting examples illustrate certain aspects of the present invention.

EXAMPLES 1 TO 4

Four (4) groups of test specimens were prepared. Each of these test specimens included a silicone polymer-based slab cut from a rectangular shaped element.

Each of the slabs had the same chemical composition, a silica reinforced, platinum-catalyzed, vinyl/hydride addition-cured polyorganosiloxane polymer. A vinyl functional benzotriazole was covalently bonded into this polymer to provide for ultraviolet light absorbance. The index of refraction of these slabs was about 1.46.

Filament haptics, made of polymethylmethacrylate were provided. Each of these haptics was constructed with no anchor structures and had a substantially uniform cross-sectional area along its length. None of the haptics were subjected to high frequency corona discharge activation or plasma activation.

A precursor composition of a cross-linked polyorganosiloxane polymer was provided. This precursor included a vinyl functional polysiloxane (base polymer), a hydride functional organohydrogensiloxane (cross-linker) and a platinum-containing catalyst. This precursor composition is substantially similar to the precursor used to provide the above-noted platinum catalyzed vinyl/hydride addition cured polyorganosiloxane.

In addition, a primer was provided and was as follows: Primer A, which is a mixture of tetra(2-methoxyethoxy)silane, tetrapropylorthosilicate, and tetrabutyltitanate in an organic liquid medium containing about 85% by weight of naphtha. This mixture is sold by NuSil Technology under the trademark CF2-135.

Haptics were secured to a number of slabs without using a primer (NO PRIMER), and to a number of other slabs using the above-noted primer (PRIMER).

In each of the NO PRIMER and PRIMER experiments, the slab was punctured with an elongated pin having a cross-sectional area about that of the coated haptic to be inserted in the slab. In each Example, the elongated pin is dipped into the precursor composition and then inserted about the same distance into the slab. The elongated pin was removed from the slab, leaving a hole into which the coated haptic is to be placed.

In each of the NO PRIMER experiments, the lens bonding region of the haptic was dipped into the precursor composition to coat this region with such composition. The coated haptic was then placed in a puncture hole of the slab. The slab, with the coated haptic inserted, was then maintained at 80° C. for 15 minutes to cure the precursor composition. Afterwards, the haptic/slab pull strength was tested as follows. Using a Chatilion Model LTCM tensile tester, the haptic was pulled from the slab, and the pull force (in grams) required to achieve this separation was recorded.

In Examples 1 and 2, each of the PRIMER experiments was conducted as follows. The lens bonding region of the haptic was dipped into Primer A for 60 seconds. Thereafter, the primer coated haptic was dried, in air at room temperature, for 1 hour. The primer coated haptic was then processed as outlined above with respect to the NO PRIMER experiments.

In Example 3, each of the PRIMER experiments was conducted as follows. The lens bonding region of the haptic was dipped into Primer A for 10 seconds. Thereafter, the primer coated haptic was dried, in air at room temperature, for 24 hours. The primer coated haptic was then processed as outlined above with respect to the NO PRIMER experiments.

In Example 4, each of the PRIMER experiments was conducted as follows. The lens bonding region of the haptic was dipped into Primer A for 60 seconds. Thereafter, the primer coated haptic was dried, in air at room temperature for 1 hour. The primer coated haptic was then processed as outlined above with respect to the NO PRIMER experiments.

Results of these experiments are summarized in the following table.

| EXAMPLE | NUMBER OF HAPTICS | MEAN PULL STRENGTH, g | STANDARD DEVIATION, % OF MEAN | INCREASE IN PULL STRENGTH[1], % |
|---|---|---|---|---|
| 1(NO PRIMER) | 10 | 70 | 11.4 | — |
| 1(PRIMER) | 10 | 85 | 9.4 | 21.4 |
| 2(NO PRIMER) | 10 | 46 | 19.6 | — |
| 2(PRIMER) | 10 | 85 | 9.4 | 84.8 |
| 3(NO PRIMER) | 10 | 66 | 6.1 | — |
| 3(PRIMER) | 9 | 90 | 5.6 | 36.4 |
| 4(NO PRIMER) | 10 | 55 | 9.1 | — |
| 4(PRIMER) | 10 | 93 | 3.2 | 69.1 |

[1]Calculated by comparing the PRIMER results and the NO PRIMER results.

These results demonstrate that the present process provides substantial increases in the pull strength of the haptic bond. For example, the PRIMER experiments provide at least about 20% increase in pull strength relative to the NO PRIMER experiments. It is important to note that this increase in haptic pull strength is achieved without sophisticated and complex processing, such as high frequency corona discharge activation or plasma activation. Moreover, no pre-formed recesses are needed in the slab in order to achieve the increased pull strength. In addition, and quite importantly, the standard deviation achieved in accordance with the present invention is reduced relative to the NO PRIMER experiments. This observation translates to the present methods providing IOLs on a more reliable and more reproducible basis relative to, for example, IOLs made from a similar method in which a primer component is not employed. Thus, not only do the present methods provide increased haptic/optic pull strengths, but such increases are achieved with reduced variability so that, in commercial application, the present methods predictably and reproducibly produce high quality IOLs.

EXAMPLES 5 TO 7

Three (3) additional groups of test specimens were prepared. Each of these test specimens included a silicone polymer-based optic or lens body molded from a precursor composition of a cross-linked polyorganosiloxane polymer combined with a silica reinforcer component and a vinyl functional benzotriazole. Each of the these optics had the same chemical composition, and included a silica reinforced platinum catalyzed vinyl/hydride addition-cured polyorganosiloxane polymer. The index of refraction of these lenses was about 1.46.

Filament haptics similar to those described in Examples 1 to 4 were provided. The configurations of the haptics used in Examples 5 and 7 were quite similar, whereas the configuration of the haptics used in Example 6 was somewhat different. In addition, a precursor composition and a primer composition, as described in Examples 1 to 4, were provided.

Haptics were secured to a number of lenses without using a primer (NO PRIMER), and to a number of other lenses using the primer composition (PRIMER).

In each of the NO PRIMER and PRIMER experiments, the lens was punctured with an elongated pin having a cross-sectional area about that of the coated haptic to be inserted in the lens. In each Example, the elongated pin was dipped into the precursor composition and then inserted about the same distance into the lens. The elongated pin was removed from the lens leaving a hole into which the coated haptic is to be placed.

Each of the NO PRIMER experiments was conducted in a manner similar to that set forth in Examples 1 to 4.

Each of the PRIMER experiments was conducted as follows. The lens bonding region of the haptic was dipped into Primer A for 60 seconds. Thereafter, the primer coated haptic was dried, in air at room temperature, for 1 hour. The primer coated haptic was then processed as outlined above with respect to the NO PRIMER experiments.

Results of these experiments are summarized in the following table.

| EXAMPLE | NUMBER OF HAPTICS | MEAN PULL STRENGTH, g | STANDARD DEVIATION, % OF MEAN | INCREASE IN PULL STRENGTH[1], % |
|---|---|---|---|---|
| 5(NO PRIMER) | 10 | 59 | 10.2 | |
| 5(PRIMER) | 10 | 69 | 8.7 | 16.9 |
| 6(NO PRIMER) | 10 | 35 | 8.6 | |
| 6(PRIMER) | 20 | 64 | 10.9 | 85.3 |
| 7(NO PRIMER) | 10 | 63 | 19.0 | — |
| 7(PRIMER) | 20 | 71 | 12.7 | 12.7 |

[1]Calculated by comparing the PRIMER results and the NO PRIMER results.

These results with optics or lenses are substantially consistent with the results described in Examples 1 to 4, using slabs rather than lenses. For example, the present methods, which involve the use of primer components, provide increased haptic/optic pull strengths relative to lenses produced without the use of such primer components. In addition, for the most part, the standard deviation with the PRIMER samples is reduced relative to the standard deviation with the NO PRIMER samples. The difference in the results between Examples 5 and 7 and Example 6 is believed to be due to the differences in haptic configuration.

In summary, the present methods are relatively straight forward, easy and inexpensive to practice, and are effective in providing IOLs which have substantially enhanced fixation member/optic pull strengths. Moreover, no exotic activation procedures are necessary to prepare the fixation members for use in the present IOLs. One important feature of the present invention is that the IOLs are produced in a very reliable and reproducible manner so that, in a commercial context, the present methods may be employed with a reduced risk of producing, and having to scrap, product which does not meet specifications.

While this invention has been described with respect to various specific examples and embodiments, it is to be understood that the invention is not limited thereto and that it can be variously practiced within the scope of the following claims.

What is claimed is:

1. A method of producing an intraocular lens including an optic and at least one fixation member having a proximal end portion located in the optic, said method comprising:

contacting the proximal end portion of a fixation member with a primary component at conditions effective to form a coated fixation member including a coating of said primer component located on said proximal end portion, said coating being effective to enhance the bond strength between said proximal end portion and a silicone polymeric object to which said proximal end portion is bonded relative to a substantially identical proximal end portion without said coating, said fixation member being subjected to no high frequency corona discharge activation or plasma activation or other exotic activation procedure;

contacting the proximal end portion of said coated fixation member with a precursor composition of a cross-linked silicone polymeric material to form a doubly coated fixation member;

forming a recess in an optic member which is pre-formed and comprises a silicone polymeric material, said recess having a size sufficient to accept the proximal end portion of said doubly coated fixation member;

placing the proximal end portion of said doubly coated fixation member into said recess; and subjecting said optic member and said doubly coated fixation member in said recess to conditions effective to cure said precursor composition of a cross-linked silicone polymeric material.

2. The method of claim 1 wherein said fixation member is made of a non-silicon-containing material.

3. The method of claim 1 wherein said primer component contacting step includes precoating the proximal end portion of said fixation member with a material comprising said primer component and a liquid medium; and thereafter removing said liquid medium from said coated fixation member.

4. The method of claim 1 which further comprises forming said optic member, and wherein said subjecting occurs at an elevated temperature effective to cure said precursor composition of a cross-linked silicone polymeric material.

5. The method of claim 4 wherein said optic member forming step comprises placing a silicon-containing precursor composition into a mold and subjecting said silicon-containing precursor composition in said mold to conditions effective to form said silicone polymeric material.

6. The method of claim 1 wherein said recess forming step comprises puncturing said optic member with a needle-like implement or a machine tool, or employing photoablation, ultrasound or a water jet.

7. The method of claim 1 which further comprises introducing a quantity of said precursor composition of a cross-linked silicone polymeric material in said recess prior to said placing.

8. The method of claim 1 wherein the proximal end portion of said coated fixation member is dried prior to said contacting step to form said doubly coated fixation member.

9. The method of claim 1 wherein the chemical make-up of said precursor composition of a cross-linked polymeric material is substantially identical to the chemical make-up of the precursor composition from which said silicone polymeric material included in said optic member is formed.

10. The method of claim 1 wherein said fixation member is made of a material selected from the group consisting of polymeric materials and mixtures thereof.

11. The method of claim 1 wherein said fixation member is made of a material selected from the group consisting of polypropylene, polyamide, polymethylmethacrylate and mixtures thereof.

12. The method of claim 1 wherein said subjecting step forms an intraocular lens assembly in which the pull strength of said fixation member is increased relative to a substantially identical intraocular lens assembly formed by a substantially identical method without said primer component contacting step.

13. The method of claim 1 wherein said subjecting step forms an intraocular lens assembly in which the pull strength of said fixation member is increased by at least about 20% relative to a substantially identical intraocular lens assembly formed by a substantially identical method without said primer component contacting step.

14. The method of claim 1 wherein said subjecting step forms an intraocular lens assembly in which the pull strength of said fixation member is increased by at least about 50% relative to a substantially identical intraocular lens assembly formed by a substantially identical method without said primer component contacting step.

15. The method of claim 1 wherein said subjecting step forms an intraocular lens assembly, and a plurality of said intraocular lens assemblies have a mean pull strength of said fixation member which is increased by at least about 20% relative to a plurality of substantially identical intraocular lens assemblies formed by a substantially identical method without said primer component contacting step, and the standard deviation from the mean pull strength in the plurality of said intraocular lens assemblies is less than about 15% of the mean pull strength.

16. The method of claim 1 wherein said subjecting step forms an intraocular lens assembly, and a plurality of said intraocular lens assemblies have a mean pull strength of said fixation member which is increased by at least about 50% relative to a plurality of substantially identical intraocular lens assemblies formed by a substantially identical method without said primer component contacting step, and the standard deviation from the mean pull strength in the plurality of said intraocular lens assemblies is less than about 10% of the mean pull strength.

17. The method of claim 1 wherein said silicone polymeric material is a polysiloxane elastomer, and said optic member further comprises an effective amount of a reinforcer component.

18. The method of claim 1 wherein said primer component is selected from the group consisting of organo silanes, organo titanium-containing components and mixtures thereof.

19. The method of claim 1 wherein said primer component is selected from the group consisting of tetrapropylorthosilicate, tetra(2-methoxyethoxy) silane, tetrabutyltitanate and mixtures thereof.

* * * * *